United States Patent [19]
Oaks

[11] Patent Number: 6,107,056
[45] Date of Patent: *Aug. 22, 2000

[54] SCTLA-4 GENE AND PRODUCT

[76] Inventor: Martin K. Oaks, 4805 Squire Dr., Greendale, Wis. 53129

[*] Notice: This patent issued on a continued prosecution application filed under 37 CFR 1.53(d), and is subject to the twenty year patent term provisions of 35 U.S.C. 154(a)(2).

[21] Appl. No.: 08/804,180

[22] Filed: Feb. 21, 1997

Related U.S. Application Data

[60] Provisional application No. 60/012,074, Feb. 22, 1996.

[51] Int. Cl.⁷ .................................................. C12P 21/06
[52] U.S. Cl. ..................... 435/69.1; 435/320.1; 536/23.1
[58] Field of Search ................................ 435/69.1, 320.1; 536/23.1

[56] References Cited

U.S. PATENT DOCUMENTS 5,434,131  7/1995  Linsley et al. .............................. 514/2

OTHER PUBLICATIONS

Gerstmayer et al, FEBS Letters, 407, 63–68, 1997.

*Primary Examiner*—David Saunders
*Attorney, Agent, or Firm*—Andrus, Sceales, Starke & Sawall

[57] ABSTRACT

The invention identifies a novel mRNA transcript in man, mouse and the rat which encodes a CTLA-4 molecule which lacks the transmembrane region, and thus represents a native soluble form of CTLA-4. This shortened CTLA-4 transcript and its predicted polypeptide product are designated sCTLA-4. The nucleotide and the predicted amino acid sequences encoding the human, rat and mouse sCTLA-4 molecules are provided.

10 Claims, 10 Drawing Sheets

```
              M   H   V   A   Q   P   A   V   V   L   A   S   S   R   G   I   A   S   F   V
ATGCACGTGGCCCAGCCTGCTGTGGTACTGGCCAGCAGCCGAGGCATCGCCAGCTTTGTG  -20
************************************************************

C   E   Y   A   S   P   G   K   A   T   E   V   R   V   T   V   L   R   Q   A
TGTGAGTATGCATCTCCAGGCAAAGCCACTGAGGTCCGGGTGACAGTGCTTCGGCAGGCT  -40
************************************************************

D   S   Q   V   T   E   V   C   A   A   T   Y   M   M   G   N   E   L   T   F
GACAGCCAGGTGACTGAAGTCTGTGCGGCAACCTACATGATGGGGAATGAGTTGACCTTC  -60
************************************************************

L   D   D   S   I   C   T   G   T   S   S   G   N   Q   V   N   L   T   I   Q
CTAGATGATTCCATCTGCACGGGCACCTCCAGTGGAAATCAAGTGAACCTCACTATCCAA  -80
************************************************************

G   L   R   A   M   D   T   G   L   Y   I   C   K   V   E   L   M   Y   P   P
GGACTGAGGGCCATGGACACGGGACTCTACATCTGCAAGGTGGAGCTCATGTACCCACCG  -100
************************************************************

P   Y   Y   L   G   I   G   N   G   T   Q   I   Y   V   I   A   K   E   K   K
CCATACTACCTGGGCATAGGCAACGGAACCCAGATTTATGTAATTGCTAAAGAAAAGAAG  -120
*******************************************_____

P   S   Y   N   R   G   L   C   E   N   A   P   N   R   A   R   M   -
CCCTCTTACAACAGGGGTCTATGTGAAAATGCCCCCAACAGAGCCAGAATGTGA
_____
```

Figure 2(a)

```
          M   A   C   L   G   L   Q   R   Y   K   T   H   L   Q   L   P   S   R   T   W
         ATGGCTTGTCTTGGACTCCAGAGGTACAAAACTCACCTGCAGCTGCCTTCTAGGACTTGG         -20
         ............................................................

P   F   G   V   L   L   S   L   L   F   I   P   I   F   S   E   A   I   Q   V
         CCTTTTGGAGTCCTGCTTTCTCTTCTCTTCATCCCAATCTTCTCTGAAGCCATACAAGTG         -40
         ..................................................*********

T   Q   P   S   V   V   L   A   S   S   H   G   V   A   S   F   P   C   E   Y
         ACCCAACCTTCAGTGGTGTTGGCCAGCAGCCACGGTGTCGCCAGCTTTCCATGTGAATAT         -60
         ************************************************************

A   S   S   H   N   T   D   E   V   R   V   T   V   L   R   Q   T   N   D   Q
         GCATCTTCACACAACACTGATGAGGTCCGGGTGACGGTGCTGCGGCAGACAAATGACCAA         -80
         ************************************************************

V   T   E   V   C   A   T   T   F   T   V   K   N   T   L   G   F   L   D   D
         GTGACAGAGGTCTGTGCCACGACATTCACAGTGAAGAACACGTTGGGCTTCCTAGATGAC         -100
         ************************************************************

P   F   C   S   G   T   F   N   E   S   R   V   N   L   T   I   Q   G   L   R
         CCCTTCTGCAGTGGTACCTTTAATGAAAGCAGAGTGAACCTCACCATCCAAGGACTGAGG         -120
         ************************************************************

A   A   D   T   G   L   Y   F   C   K   V   E   L   M   Y   P   P   P   Y   F
         GCTGCTGACACCGGACTGTACTTCTGCAAGGTGGAACTCATGTACCCACCGCCATACTTT         -140
         ************************************************************

V   G   M   G   N   G   T   Q   I   Y   V   I   A   K   E   K   K   S   S   Y
         GTGGGCATGGGCAACGGGACCCAGATTTATGTCATCGCTAAAGAAAAGAAGTCCTCTTAC         -160
         ***************************************_____

N   R   G   L   C   E   N   A   P   N   R   A   R   M   -
         AACAGGGGTCTATGTGAAAATGCCCCCAACAGAGCCAGAATGTGAAAAGCAATTTCAACC
         _____

TTATTTTATTCCAATCAACTGAAAGGCCATTTGTGAAGAAGAGGGAGCATTCTTCAGTCT         -600

CTAAAAGCTGAGGC
```

Figure 2(b)

```
MACLGLQRYKTHLQLPSRTWPFGVLLSLLFIPIFSEAIQVTQPSVVLASSHGVASFPCEYASSHN
MACLGLQRYKTHLQLPSRTWPFGVLLSLLFIPIFSEAIQVTQPSVVLASSHGVASFPCEYASSHN
................................******************************

TDEVRVTVLRQTNDQVTEVCATTFTVKNTLGFLDDPFCSGTFNESRVNLTIQGLRAADTGLYFCK
TDEVRVTVLRQTNDQVTEVCATTFTVKNTLGFLDDPFCSGTFNESRVNLTIQGLRAADTGLYFCK
****************************************************************

VELMYPPPYFVGMGNGTQIYVI                                      AKEKKS
VELMYPPPYFVGMGNGTQIYVIDPEPCPDSDFLLWILAAVSSGLFFYSFLVTAVSLNRTLKKRSP
**********************--------------------------------------____

SYNRGLCENAPNRARM
LTTGVYVKMPPTEPECEKQFQPYFIPIN
```

Figure 3

```
HUMAN                                               MH*AA****R*
RAT    MACLGLQRYKTHLQLPSRTWPFGVLLSLLFIPIFSEAIQVTQPSVVLASSHG

HUMAN  I***V*****PGKAT**********ADS*******A*YMMG*E*T****SI*T
RAT    VASFPCEYASSHNTDEVRVTVLRQTNDQVTEVCATTFTVKNTLGFLDDPFCS

MOUSE                  ***********************
HUMAN  SSGNQ******M**I*********YL*I*************
RAT    GTFNESRVNLTIQGLRAADTGLYFCKVELMYPPPYFVGMGNGTQIYVIAKEK

MOUSE  *****************
HUMAN  *P***************
RAT    KSSYNRGLCENAPNRARM
```

Figure 4

```
    I   Y   V   I ↓                (≈0.5 Kb)                 ↓ D   P   E   P
ATTTATGTCATCGgtaagcagagccattcc..........ttttgtgttgcagATCCAGAACCA
    I   Y   V   I                  INTRON A C   P   D   S   D   F   L   L   W   I   L   A   A   V   S   S   G   L   F   F   Y
TGCCCAGATTCAGACTTCCTCCTTTGGATCCTTGCTGCAGTTAGTTCGGGGTTGTTTTCTAC S   F   L   V   T   A   V   S   L   N   R   T ↓       (≈1.1 Kb)
AGTTTCCTGGTCACCGCTGTTTCTTTGAACAGGACGgtgagtgt..........tcttttgtg
                                                            INTRON B
        ↓ L   K   K   R   S   P............
tttttggcagCTAAAGAAAAGAAGTCCT
          A   K   E   K   K   S............
```

Figure 5

SCTLA-4 GENE AND PRODUCT

CROSS-REFERENCE TO RELATED APPLICATIONS

This Application claims priority to Provisional Application Ser. No. 60/012,074 filed on Feb. 22, 1996.

STATEMENT REGARDING FEDERALLY SPONSORED RESEARCH OR DEVELOPMENT

N/A

BACKGROUND OF THE INVENTION

The interactions of T lymphocytes with antigen presenting cells (APC) are central to the generation of an immune response to foreign pathogens, transplanted organs, and self-antigens in the setting of autoimmune disease. The specificity of these interactions is provided by recognition of an antigen on the APC by the T cell antigen receptor (TCR). TCR engagement alone does not generally lead to full T cell activation, but instead may lead to T cell unresponsiveness (anergy). A successful immune response requires additional interactions between the T cell and APC. These so-called "costimulatory" interactions thus determine the outcome of TCR engagement; that is, whether this engagement activates or inactivates subsequent immune responses. It is now clear that a key T cell costimulatory signal is provided by interaction of CD28 receptors on T cells with B7 counter-receptors on APC. Like CD28, CTLA-4 is a second receptor for B7 molecules; however, it has a higher avidity for B7 molecules than does CD28. Interference with CD28/CTLA-4:B7 interactions may thus represent a novel approach to regulating the interactions of the cells that have these receptors. The use of a native soluble form of CTLA-4 may thus serve as a immunoregulatory agent.

Other investigators have used a CTLA-4 fusion protein (the extracellular domain of the membrane form of CTLA-4 fused to a human immunoglobulin heavy chain gene) called CTLA-4Ig to regulate CD28/CTLA-4:B7 interactions. Potential limitations of this approach include unnatural tissue distribution of this entity as well as unnatural pharmacokinetics of the molecule when compared to the molecule described in the present invention.

CTLA-4 is a lymphocyte cell surface receptor originally discovered in a search for molecules having a role in T cell cytotoxicity. Although originally identified as a cytolytic T cell-associated molecule, CTLA-4 expression has been detected in both activated CD4 and CD8 T-cell populations as well as B-cells with the use of monoclonal antibodies. CTLA-4 is a member of the immunoglobulin superfamily and is highly homologous to another T cell surface receptor, CD28. Both CD28 and CLTA-4 bind the same ligands; namely, members of the B7 family of molecules expressed on antigen presenting cells. Expression of CTLA-4 is highly activation dependent. With activated T cells, maximal CTLA-4 protein expression is ~2–3% of CD28. Recombinant forms of CTLA-4 bind CD80 (B7.1) and CD86 (B7.2) with higher avidity (>20-fold) than soluble CD28. Thus, CTLA-4 is a high avidity, low abundance receptor for B7 molecules.

Much of the study of the interactions of CTLA-4 and B7 counter-receptors have relied on the use of recombinant soluble form of CTLA-4 (called CTLA4-Ig). CTLA4-Ig is a fusion protein consisting of the Ig-like extracellular domain of CTLA-4 and the human IgG heavy chain constant region gene. The presence of the IgG chain permits secretion of the recombinant protein from transfected cells, as well as enhancing purification of the molecule. Numerous reports have documented the usefulness of CTLA4-Ig as an immunoregulatory agent. For example, CTLA4-Ig inhibits alloreactivity in the content of both the mixed leukocyte reaction and in vivo in experimental cardiac allografts and pancreatic islet xenografts. CTLA-Ig is also reported to modify the course of several animal models of human disease including murine lupus, experimental autoimmune encephalomyelitis, allergic contact dermatitis, and autoimmune and anti-glomerular basement membrane glomerulonephritis. In addition, CTLA4-Ig also inhibits cellular and humoral responses to conventional antigens such as keyhole-limpet hemocyanin, sheep red blood cells, and pigeon cytochrome c.

It would be extremely useful to obtain expression of a native soluble protein product of the CTLA-4 gene. The soluble product could then be used to regulate T cell and/or B cell responses in vivo to treat pathological conditions.

The molecular cloning and the nucleotide sequence of the full length rat CTLA-4 gene has been reported. In addition to the expected target CTLA-4 transcript, distinct smaller amplification products were also observed following reverse transcriptase polymerase chain reaction (RT-PCR) of a variety of lymphoid tissues from man, mouse, and rat. The nucleotide and the predicted amino acid sequence of these alternative transcripts are described below. See Sequence ID Nos. 1–6. In addition, it will be shown that the variant transcript is most abundant in cells from bone marrow, blood, and lymph node; whereas, the transmembrane form of the molecule is the predominant, and perhaps the only species expressed in the adult thymus.

BRIEF SUMMARY OF THE INVENTION

The present invention relates to the description of an isolated and purified truncated form of the CTLA-4 gene and the corresponding CTLA-4 protein.

BRIEF DESCRIPTION OF THE DRAWINGS

In the drawings:

FIG. 2(a) is a nucleotide and predicted amino acid sequence of the human sCTLA-4 transcript.

FIG. 2(b) is the nucleotide and predicted amino acid sequence of the rat sCTLA-4 gene.

FIG. 3 is a comparison of the predicted amino acid sequences of the sCTLA-4 and the transmembrane form of rat CTLA-4.

FIG. 4 is a comparison of the predicted amino acid sequences of the rat, human, and mouse sCTLA-4 molecules.

FIG. 5 is the intron/exon boundaries of genomic DNA of the rat CTLA-4 gene.

DETAILED DESCRIPTION OF THE INVENTION

Figure 1A:
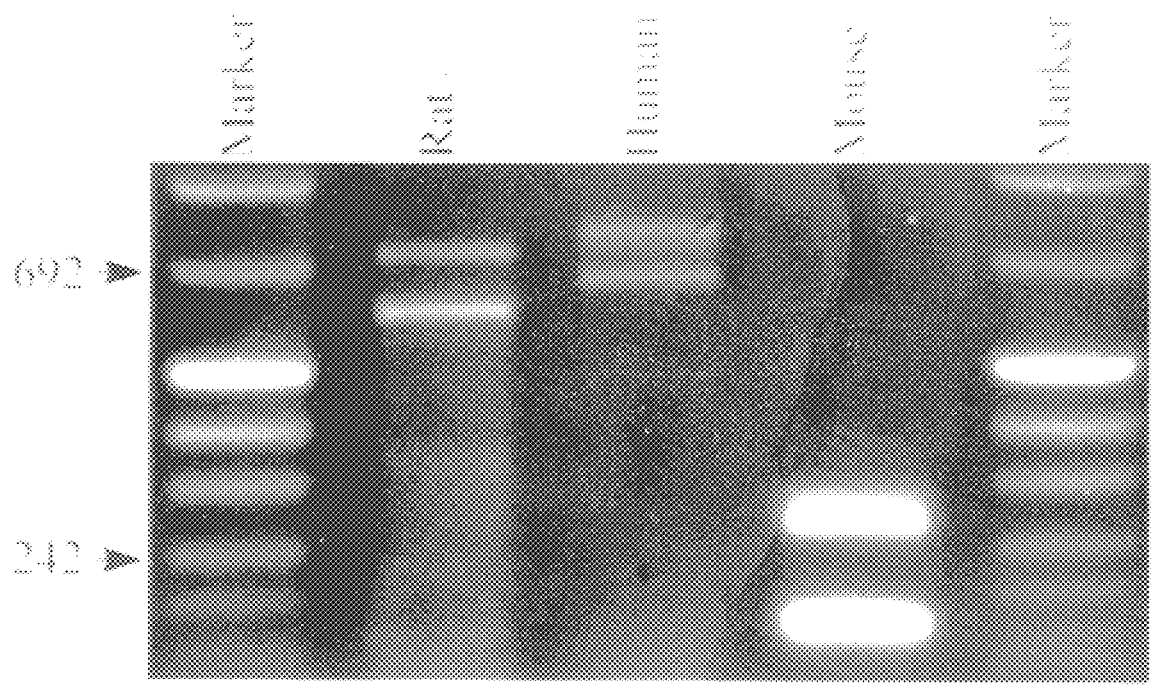
FIG. 1(a) is a photograph of an electrophoresis gel of RT-PCR products of rat, human and mouse mRNAs with CTLA-4 primers.

Tissue Samples and Cells. Female ACI rats (150–200 g) and Balb/c mice were obtained from Harlan Sprague-Dawley (Indianapolis, Ind.). The animals were housed in accordance with institutional guidelines and given rodent chow and tap water ad libitum. Human blood samples were obtained from healthy volunteers. Human adult lymph node and spleen samples, and neonatal thymus were obtained at autopsy. Mononuclear cells were obtained from spleen and blood by standard ficoll-hypaque density gradient centrifugation. Other organs and tissues were frozen and stored in liquid nitrogen until used for RNA extraction. Human PBMCs were activated for 48 hours in vitro by culture in Dulbecco's Modified Eagles' Medium containing 10% FBS, 5 μg/mL Con A and 10 nM PMA (both from Signma Chemical Co., St. Louis, Mo.). Rat $CD4^+$ and $CD8^+$ splenic lymphocytes were isolated by usual rounds of affinity chromatography (Cellect immunocolumns, Biotex Labs, Edmonton, Alberta) according to the manufacturer's instructions. B cells were negatively selected by dual passage over a T cell chromatography column, followed by immunomagnetic positive selection with the use of anti-CD45RA/B (clone OX-33). The purity of these suspensions was examined by flow cytometry using anti-CD4 and anti-CD8 monoclonal antibodies (clones OX-35 and OX-8, respectively). Less than 2 fluorescence events per 200,000 ungated cells were present in these enriched populations demonstrating the high enrichment of the cells used for RT-PCR amplification. The antibodies used in these studies were purchased from Pharmingen Corp, San Diego, Calif.

Nucleic Acid Isolation. Total cellular RNA was extracted by the guanidine thiocyanate method using kit-supplied reagents (RNAgents, Promega Biotec, Madison, Wis.). The resultant nucleic acids were resuspended in 10 mM Tris-HCl (pH 8.4), and contaminating DNA was digested in the presence of 80 U/ml RNase inhibitor (Promega) and the addition of IU RQ-1 DNase (Promega). DNase digestion was performed for 30 minutes at 37° C., and the DNase was heat-killed at 75° C. for 15 minutes. The RNA was precipitated overnight at −20° C. as described above, and the resultant pellet was washed in 75% ethanol and air dried. The dried pellet was dissolved in 25 μL water and RNA was quantified by spectrophotometry and adjusted to 200 ng/μL in water. The RNA was reverse transcribed immediately or stored at −80° C. Genomic DNA was extracted with the use of a commercially available chromatography resin (Qiagen Corp, Chatsworth, Calif.).

RT-PCR. PCR was carried out utilizing standard PCR methodology. Specifically, single-strand cDNA was generated from 1 μg total cellular RNA with the use of Superscript II pre-amplification reagents (Life Technologies, Bethesda, Md.) according to the manufacturers instructions. PCR was carried out in 25 μL volumes of 1×PCR buffer {60 mM Tris-HCl (pH 9.0), 15 mM $(NH_4)_2SO_4$, 2.5 nM $MgCl_2$} containing the 1/10 the contents of the reverse transcription reaction, 0.2 nM each dNTP, 0.5 μM each primer, and 0.05 U/μL Taq DNA polymerase (Promega, Madison, Wis.). The reactions were subjected to 20–35 amplification cycles on a Perkin Elmer-Cetus thermal cycler. The amplification cycle profile was 95° C. denaturation for 1 minute, followed by primer annealing at 60° C. and extension at 72° C. for 1 minute each. PCR products were separated by gel electrophoresis and analyzed with a Gel-Doc 1000 system equipped with Molecular Analyst software (Bio-Rad Instruments).

Oligonucleotide Primers. Primers were designed with the aid of commercially available software (Primer Designer; S&E Software, State Line, Pa.) from previously published sequences of rat, mouse, and human CTLA-4 genes. The following are the 5'→3' sequences of the sense (s) and antisense (as) primers used in these studies: RCTLA4-57s=CATGGCTTGTCTTGGACTCC SEQ ID NO: 7; RCTLA4-781as=GCCTCAGCTTTTAGAGACTG SEQ ID NO: 8; HCTLA4-4s=TTCCTGAAGACCTGAACACC SEQ ID NO: 9; HCTLA4-766as=AGAATTGCCTCAGCTCTTGG SEQ ID NO: 10; RCTLA4-366s=TGACACCGGACTGTACTTCT SEQ ID NO: 11; HCTLA4-341s=TCACTATCCAAGGACTGAGG SEQ ID NO: 12; RHCTLA4-635as=TCACATTCTGGCTCTGTTGG SEQ ID NO: 13. The size of the amplification products from cDNA derived from the transmembrane (TM) and the variant transcript described in this communication are as follows 27s/781 as rat primer set yields a 724 bp TM fragment, 614 bp sCTLA-4 fragment; 4s/766as human primer set yields a 762 bp TM fragment, and a 652 bp sCTLA-4 fragment. 366s/635as mix yields TM and sCTLA-4 fragments of 269 bp and 159 bp respectively using rat cDNA as a template. The 341s/635 primer set yields TM product of 294 bp and sCTLA-4 product of 184 bp with human cDNA as a template. Note that the 635as oligonucleotide is used as a common anti-sense primer for both rat and human cDNAs, as this sequence is derived from the highly conserved cytoplasmic domain of CTLA-4. All primers were synthesized by Operon Technologies (Alameda, Calif.).

Cloning and Sequencing. PCR product was cloned into pCR3 vector using a TA cloning kit (Invitrogen Corp., Calif.). Miniprep DNAs were prepared by the use of Wizard chromatography resin (Promega) and analyzed for the presence of the appropriately sized insert by restriction mapping. PCR products as well as cloned inserts were sequenced bi-directionally by di-deoxy cycle sequencing using the above described PCR primers and vector primers, respectively.

In order to characterize the rat and human CTLA-4 mRNAs, cellular RNA from splenocytes of ACI rats, and lymph node from humans was isolated. The CTLA-4 mRNA transcripts were then analyzed by RT-PCR amplification with the use of oligonucleotide primers that flanked the ATG initiation codons and the termination codons. The amplified products were expected to encompass the entire translation region as well as a portion of the 5' untranslated region of the CTLA-4 gene and to be 724 bp and 762 bp for rat and human, respectively.

In addition to the aforementioned full-length CTLA-4 cDNA fragments, a distinct smaller 614 bp amplification product was also observed in rats, and a 652 bp fragment was found in humans (see FIG. 1(a) ). FIG. 1(a) illustrates rat and human PCR products from spleen cDNAs amplified with primers designed to amplify the coding region of CTLA-4. Mouse products are from spleen cDNA amplified with primers that flank the CTLA-4 TM region. The upper bands in each lane represent amplifications of the CTLA-4 TM transcript, the lower bands are amplifications of the novel sCTLA-4 transcript.

Figure 1B:
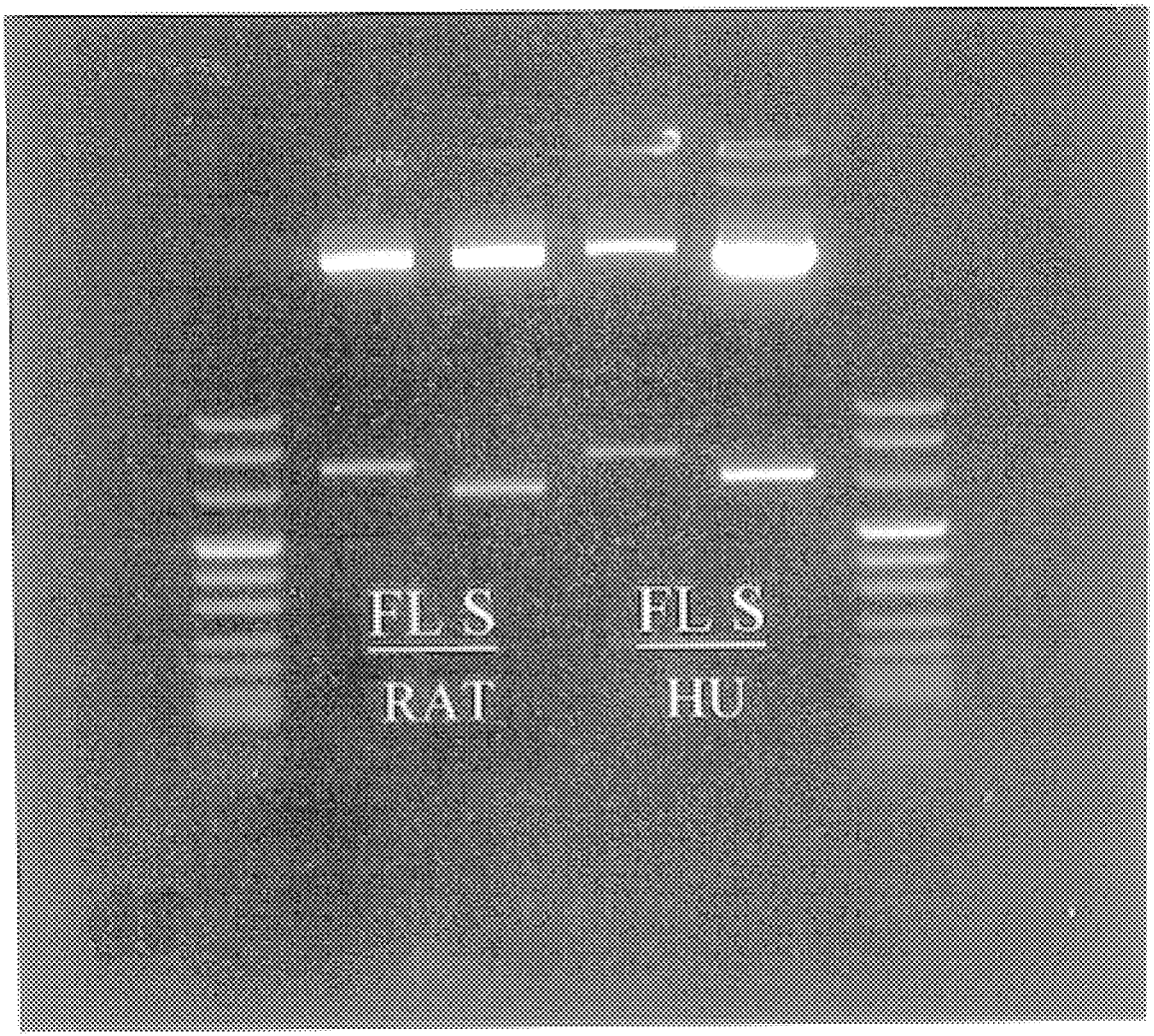
FIG. 1(b) is a photograph of an electrophoresis gel of recombinant plasmids containing inserts of the rat and human sCTLA-4 gene.

Screening of cloned PCR products also revealed recombinant clones of similar sizes (see FIG. 1(b)), and restriction enzyme analysis showed the absence of two restriction enzyme sites based on the nucleotide sequences of full length CTLA-4 within the transmembrane region of CTLA-4. The upper bands denote recombinant plasmids that contain the full length CTLA-4 gene, the lower bands denote recombinant plasmids containing the sCTLA-4 gene. Similar findings were also observed upon RT-PCR of RNA from mouse splenocytes when amplified with primers that flank the transmembrane region of CTLA-4. These data suggest that these molecules represent alternative transcripts of the CTLA-4 molecule that lack a transmembrane domain resulting in solubility.

Nucleotide sequencing of these cDNAs proved this correct. The nucleotide and predicted amino acid sequence of the mature human sCTLA-4 molecule is presented in FIG. 2(a), and the nucleotide and amino acid sequence of the mature rat sCTLA-4 gene is shown in FIG. 2(b). Asterisks (***), in FIGS. 2(a) and 2(b) illustrate the "extracellular" V domain and dashes (____) show the coding region remnants of cytoplasmic domain. Bolded amino acids represent predicted N-linked glycosylation sites. The predicted sCTLA-4 molecule (minus the leader peptide) is an 137 amino acid polypeptide, and is 49 amino acids shorter than the full-length molecule. When compared to their full-length counterparts, rat and human molecules have identical nucleotide and predicted amino acid sequences spanning their entire extracellular domains, but the sCTLA-4 form represents a deletion of the entire transmembrane domain. The nucleotide sequences of the "cytoplasmic" domains of each species are identical to their full-length counterparts with the exception of the first codon. The net effect of this is that the frameshift caused by this deletion changes the reading frame of the molecule, and thus, the amino acid sequence of the cytoplasmic domain of the sCTLA-4 molecules.

A comparison of the rat sCTLA-4 molecule to its transmembrane counterpart is presented in FIG. 3. sCTLA-4 sequence is shown on top line; transmembrane form is shown below. The two forms of CTLA-4 share identical leader peptides as well as the Ig superfamily-like V region (extracellular domain of the transmembrane polypeptide). The soluble form of CTLA-4 represents a deletion of 37 amino acids corresponding to the transmembrane region of the cell surface molecule. The carboxyl terminal 22 amino acids of sCTLA-4 represent novel amino acids when compared with the transmembrane of the molecule because of the frameshift mutation created by the intron/exon splicing that forms the sCTLA-4 alternative transcript. This frameshift mutation also creates an earlier termination codon; thus, sCTLA-4 is 12 amino acids shorter in the tail region when compared to the transmembrane molecule.

The dots (...) in FIG. 3 illustrate the signal sequence; asterisks (***) represent the V-like extracellular domain; dashes (---) illustrate the transmembrane region; the line (____) shows the cytoplasmic tail. Bolded amino acids represent predicted sites for N-linked glycosylation. This alternative transcript is also found in mouse splenocyte RNA, and has identical splice sites when compared to the rat and human sCTLA-4 molecules.

FIG. 4 is a comparison of the amino acid sequences of the predicted sCTLA-4 polypeptides from man, mouse, and rat. Asterisks (*) in FIG. 4 indicate amino acid identity when compared to the rat sequence. The dots (...) show the signal peptide; dashes (---) illustrate the immunoglobulin V-region; The line (____) shows vestiges of cytoplasmic tail. Note that there is 100% conservation in the amino acid sequence of the vestige of the cytoplasmic tails of mouse and rat sCTLA-4, and 95% conservation between human and mouse or rat. The sCTLA molecules from all three species contain the MYPPPY peptide motif found in the V-like domain of rat, mouse, and human CTLA-4. The conservation of this motif is important because it is critical to the binding of CTLA-4 to B7 family molecules; thus, its presence in rat predicts a lack of species specificity for B7:sCTLA-4 binding. Furthermore, their presence predicts that the predicted sCTLA-4 protein would have B7 binding properties. The human and rat sCTLA-4 molecules are predicted to have 2 and 3 N-linked glycosylation sites, respectively, based upon the presence of the Asn-X-Ser/Thr motifs. The membrane proximal cysteine (amino acid 120 in the human numbering system), which appears to be responsible for the formation of homodimers in the TM CTLA-4 protein, is absent in the sCTLA-4 molecule, although a novel cysteine residue is created within the vestige of the cytoplasmic domain. Thus, it is possible that the predicted sCTLA-4 molecule also exists as a dimer.

In order to determine whether sCTLA-4 arose by translation of an alternatively spliced transcripts, genomic DNA surrounding the TM-encoding regions of rat CTLA-4 was amplified by PCR and cloned. Restriction enzyme analysis of the cloned genomic DNA revealed two introns. Intron A is approximately 500 bp and lies between the extracellular and TM exons; intron B is approximately 1100 bp, and resides between the TM and cytoplasmic domain exons. DNA sequencing of the splice donor/acceptor (SD and SA respectively) sites adjacent to the intron/exon boundaries predicts two possible transcripts of the CTLA-4 molecule based on consensus sequences of SD/SA sites (see FIG. 5). ↓ of FIG. 5 indicates location of nucleotide at intron/exon boundary. Upper case nucleotides denote exons, lower case denotes introns. Splices between the SD/SA sites of both introns A and B produces the transcript encoding the transmembrane form of the molecule (amino acid sequence shown above nucleotide sequence). A splicing event between the SD site of intron A and the SA site of intron B produces the soluble form of CTLA-4. The amino acid sequence of sCTLA-4 is shown below the nucleotide sequence. Note that the A→B splice results in a deletion of the transmembrane encoding exon as well as a frame shift mutation that results in a novel amino acid sequence within the final exon of CTLA-4. The transmembrane form on the molecule arises via two RNA splicing events between the SD/SA sites of intron A as well as between the SD/SA sites of intron B. By application of the same rules for SD/SA splicing, splicing of the intron A donor site to the intron B acceptor site would accurately yield the sCTLA-4 transcript. The net effect of this splicing event is a 110 bp deletion corresponding to the entire transmembrane domain of the CTLA-4 molecule. The A→B splicing event also introduces a frameshift mutation throughout the "cytoplasmic" domain of sCTLA-4 (the alternative reading frame of each are illustrated in FIG. 5). Thus although the nucleotide sequences of these molecules are identical downstream of the splice sites, the change in reading frame produces an amino acid tail that is unique to the sCTLA-4 molecule. This tail is 22 amino acids long and 12 amino acids shorter than that of the transmembrane form of CTLA-4 due to the introduction of a TGA termination codon at nucleotide position 523 of the rat sCTLA-4 gene. The genomic structure of the human CTLA-4 gene is highly similar, and examination of the sequences of the SD/SA sites predicts the possible presence of the described sCTLA-4 transcript.

Figure 6A:
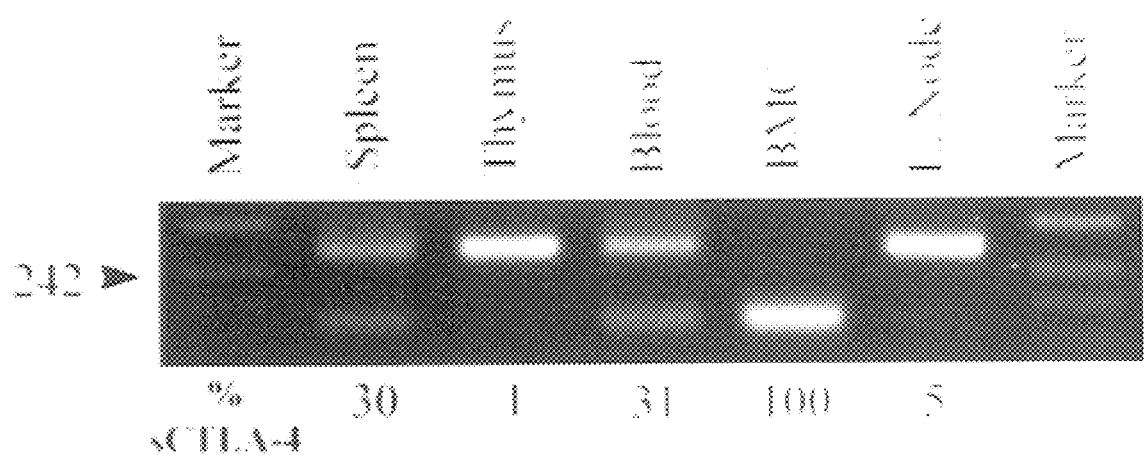
FIG. 6(a) is a photograph of an electrophoresis gel illustrating the tissue distribution of the sCTLA-4 transcript in rats.

In order to examine the tissue distribution of the TM and sCTLA-4 transcripts, RT-PCR with primers that flank the TM region of CTLA-4 were used. Because both transcripts compete for the same oligonucleotide primers during PCR, the relative levels of each transcript can be estimated from their fluorescent intensities on an ethidium bromide stained gel. The results of a typical experiment are shown on FIG. 6(a). The electrophoresis gel is of PCR products using primers that surround the transmembrane region of rat CTLA-4. The upper band is approximately 269 bp, and corresponds to the TM form of the CTLA-4 molecule; the lower band is approximately 159 bp which is consistent with the size of a putative sCTLA-4 molecule. The arrow indicates a marker band of 242 bp.

Both the TM and sCTLA-4 transcripts were detected in lymph node, spleen, and peripheral blood in both man and the rat. The TM transcript appears to be the only transcript expressed in the thymus of adult rats; whereas the sCTLA-4 transcript is the only mRNA species detected in bone marrow cells. The expression of both CTLA-4 transcripts appears to be exclusive to the hematolymphoid system and neither CTLA-4 TM nor sCTLA-4 were detected in a wide variety of non-lymphoid tissues including adrenal, brain, eye, heart, kidney, liver, lung, ovary, pancreas, salivary gland, seminal vesicles, skeletal muscle, testes, and thyroid (data not shown).

Figure 6B:
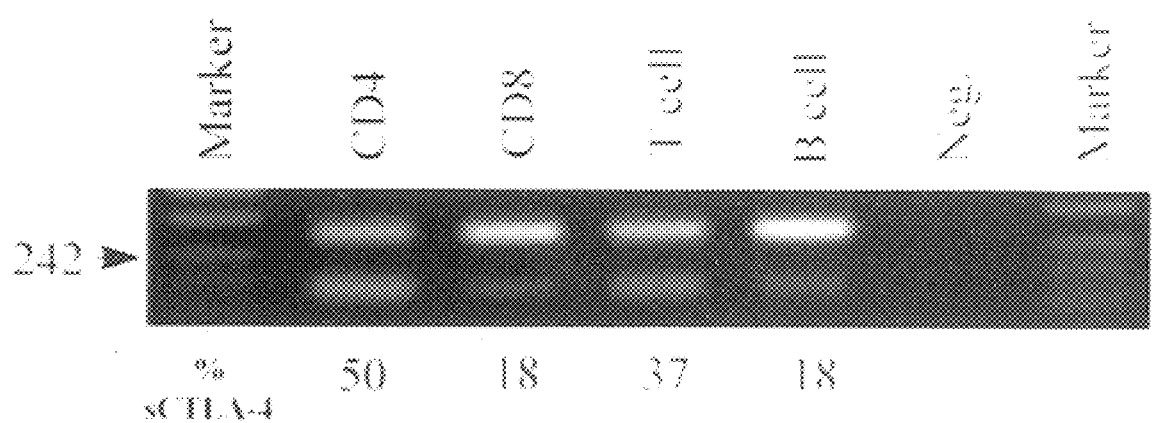
FIG. 6(b) is a photograph of an electrophoresis gel illustrating expression of CTLA-4 in rat lymphoid subsets.

The distribution of the TM and sCTLA-4 transcripts within lymphocyte subsets was also determined. RNA from highly enriched lymphocyte populations was subjected to RT-PCR using primers that span the TM region of CTLA-4. The arrow indicates a 242 bp marker. The "Neg" lane is product from RT-PCR reaction mix minus cDNA. As demonstrated in FIG. 6(b), both the TM and sCTLA-4 transcripts are expressed in the CD4 and CD8 subsets of T cells, as well as B lymphocytes. The relative amounts of the TM and sCTLA-4 transcripts appear to differ between the CD4 and CD8 T cell subsets. For example, in the CD4 subset, nearly identical amounts of each amplified product, whereas their appears to be nearly 2.5-fold more TM transcript than sCTLA-4 transcript among CD8+ T cells. This skewed distribution of CTLA-4 transcripts among the CD4 and CD8 populations produces a TM:sCTLA-4 ratio of approximately 1.5:1 when analyzed as unfractionated T cells. The TM CTLA-4 species is the predominant transcript among B-cells, representing 71% of the total CTLA-4 amplification product in this experiment. By contrast, the relative amount of TM and sCTLA-4 transcripts among unfractionated T cells is 59% vs. 41%, respectively. Similar data were obtained in a duplicate set of experiments.

Soluble forms of receptors are produced through proteolytic cleavage of membrane-bound receptors such as in the case of the tumor necrosis factor receptor and the interleukin-2 receptor or by translation of alternative spliced mRNA as found in the IL-4, IL-7, and FAS receptors. Such secreted receptors represent truncated forms of the membrane-bound receptors because of the introduction of a frameshift or stop codons. These soluble receptors can bind ligand in a similar manner as their membrane-bound counterparts and as a result may play an important role in the regulation of receptor activity. The data presented suggest that like many other receptors with immunoregulatory function, it has been found a CTLA-4 receptor also exists as a truncated form. When compared to the transmembrane form of the CTLA-4 molecule, the sCTLA-4 transcript appears to be more predominant in resting cells than in activated cells. This finding may explain why this mRNA species has not previously identified, as CTLA-4 is widely considered an activation antigen, and thus, most studies of CTLA-4 expression are performed on activated cells.

Figure 7:
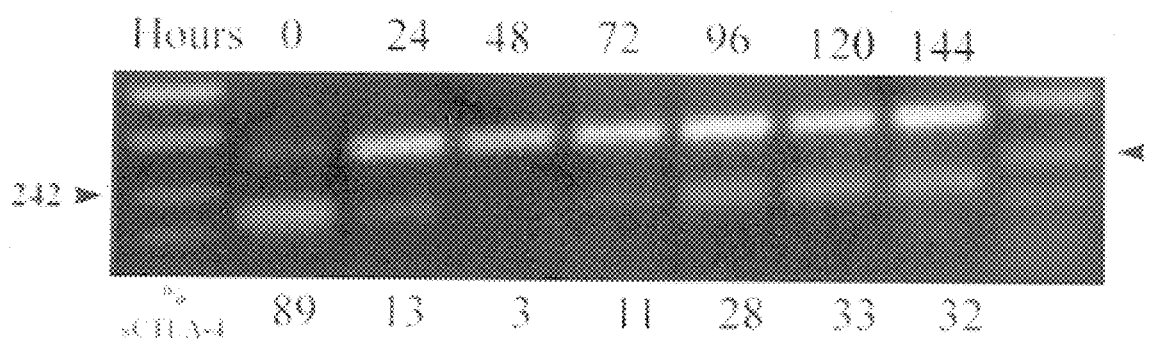
FIG. 7 is a photograph of a electrophoresis gel showing the effects of activation status on the relative levels of TM vs sCTLA-4 mRNA.

Because the mRNA and protein product of the CTLA-4 gene are reported to be expressed on activated but not resting T cells, it was attempted to determine the relative levels of CTLA-4 gene reported to be expressed on activated but not resting T cells. It was also attempted to determine the relative levels of CTLA-4-TM versus sCTLA-4 on resting and activated human PBMC's by RT-PCR. The results of a representative experiment are shown in FIG. 7. Human PBMCs were activated for the indicated time periods as previously described and harvested for RT-PCR analysis using primers that span the TM region of the CTLA-4 gene. The upper lane indicates a 294 bp product of the TM CTLA-4 transcript; the lower lane indicates a 184 bp product of the sCTLA-4 transcript. Although both transcripts are detected in resting cells, the sCTLA-4 transcript appears to be the predominant one. This ratio is reversed by 24 hours post-activation, and by 48 hours CTLA-4 TM is almost the exclusive mRNA transcript. From 72–120 hours following activation, the sCTLA-4 transcript appears to increase relative to CTLA-4 TM, although it does not exceed about ⅔ of the total CTLA-4 mRNA. Similar results were obtained upon activation of either at or human PBMC with anti-CD3+ anti-CD28 (not shown)

Attempts to express recombinant sCTLA-4 in a variety of mammalian cells have been thus far unsuccessful. It is thought that failures in this regard are related to post-translational and/or post-translational regulation, as polyadenylated mRNA is readily detected in transfected cells (data not shown). Furthermore, the rat sCTLA-4 transcript is readily translated in vitro, and produces the predicted 19 kDa polypeptide. Like sCTLA-4, the transmembrane form of the molecule has been difficult to express in transfected cells. However, the difficulties experienced in expressing the TM form of CTLA-4 have largely been attributed to an 11 amino acid tyrosine-containing motif in the highly conserved cytoplasmic domain of CTLA-4 which appears to act as a Golgi or post-Golgi retention signal. This would appear not to be the case with the sCTLA-4 variant because the frameshift caused by the use of alternative splice sites creates a novel amino acid sequence when compared to the cytoplasmic domain of the TM form of CTLA-4. However, one can not rule out the possibility that the novel amino acid sequence formed by the vestige of the cytoplasmic domain of CTLA-4 also encode retention sequences.

It is believed unlikely that the sCTLA-4 transcript shown in the various electrophoresis gels represents an artifact that was amplified during PCR. First, cellular activation appears to regulate the relative levels of each CTLA-4 transcript, as the sCTLA-4 variant appears to be the predominant transcript in resting peripheral blood leukocytes, whereas the TM form is the predominant species by 24–48 hours post-activation (see FIG. 7). In addition, the relative levels of each transcript appear to vary by cell type. For example, among T cells the relative levels of each CTLA-4 mRNA species are nearly equivalent; whereas the TM species is the predominant one within B-cells. Thirdly, the SA/SD sites at the intron/exon boundaries of the extracellular and cytoplasmic domains of the sCTLA-4 molecule more closely fit the classical rules for intron/exon splicing. Perhaps more importantly, lymphoid tissues appear to express varying relative amounts of each transcript. For example, the TM form appears to be the only transcript expressed in the thymus, but the sCTLA-4 transcript is the predominant species in bone marrow cells. It is thus difficult to envision a scenario by which errors in splicing would be differentially regulated in different lymphoid compartments as well as by activation status.

In summary, the identification isolation and purification of a novel transcript of the CTLA-4 gene in man, the mouse, and the rat has been performed. The fact that this transcript lacks the entire membrane-spanning domain of the classical CTLA-4 molecule suggests that it encodes a native soluble form of the CTLA-4 molecule. Because the amino acid residues that are thought to be critical to B7 molecule binding (namely the MYPPPY motif are intact, the expression of this molecule encodes a novel protein capable of binding the B7 family of molecules. The consequences of B7 molecule binding of the membrane forms of CD28 and CTLA-4 appear to be opposing. It is well established that B7:CD28 interactions provide a major costimulatory signal to T cell activation. The emerging notion of B7:CTLA-4 binding is that CTLA-4 triggering provides a negative signal to T cells, and in fact may lead to apoptosis and/or a state of immunologic anergy. In this context, one can envision a dual role for the candidate sCTLA-4 molecule. On one hand, sCTLA-4 may bind B7 expressing APC and thus interfere with B7:CD28 mediated costimulation of T cell responses. On the other hand, sCTLA-4 may also be capable of interfering with B7:CTLA-4 interactions, thus blocking the negative signal imparted via the TM form of CTLA-4. Verification of this hypothesis awaits identification of the protein product of the sCTLA-4 transcript.

The possibility that recombinant sCTLA-4 could be used to regulate with B7:CD28 interactions is raised by the aforementioned data. In this context, CTLA-4-Ig has been highly successful in regulating the in vivo and in vitro immune response to a wide variety of antigens. Expression of the sCTLA-4 gene may produce a natural soluble form of CTLA-4 with similar useful immunoregulatory properties.

I claim:

1. An isolated and purified nucleic acid sequence having the nucleic acid sequence set forth in Sequence ID Number 1.

2. An isolated and purified nucleic amino acid sequence having the nucleic acid sequence set forth in Sequence ID Number 3.

3. An isolated and purified nucleic acid sequence having the nucleic acid sequence set forth in Sequence ID Number 5.

4. A recombinant plasmid comprising a DNA sequence selected from the group consisting of the nucleic acids having the sequences described in Sequence ID Numbers 1, 3 and 5.

5. A recombinant DNA expression vector which comprises in operable linkage, an enhancer sequence, a promoter sequence, and at least one gene having the nucleotide sequence set forth in Sequence ID Number 1.

6. A recombinant DNA expression vector which comprises in operable linkage, an enhancer sequence, a promoter sequence, and at least one gene having the nucleotide sequence set forth in Sequence ID Number 3.

7. A recombinant DNA expression vector which comprises in operable linkage, an enhancer sequence, a promoter sequence, and at least one gene having the nucleotide sequence set forth in Sequence ID Number 5.

8. A method for producing sCTLA-4 by expression of a gene encoding an sCTLA-4 protein which comprises the steps of transforming a host cell with an expression vector containing an sCTLA-4 gene having the nucleotide sequence of Sequence ID Number 1 operably linked to an effective promoter and transcription terminator, growing said transformed host cell and isolating said sCTLA protein produced.

9. A method for producing sCTLA-4 by expression of a gene encoding an sCTLA-4 protein which comprises the steps of transforming a host cell with an expression vector containing an sCTLA-4 gene having the nucleotide sequence of Sequence ID Number 3 operably linked to an effective promoter and transcription terminator, growing said transformed host cell and isolating said sCTLA protein produced.

10. A method for producing sCTLA-4 by expression of a gene encoding an sCTLA-4 protein which comprises the steps of transforming a host cell with an expression vector containing an sCTLA-4 gene having the nucleotide sequence of Sequence ID Number 5 operably linked to an effective promoter and transcription terminator, growing said transformed host cell and isolating said sCTLA protein produced.

* * * * *

```
                         SEQUENCE LISTING (1) GENERAL INFORMATION:

(iii) NUMBER OF SEQUENCES:  13

(2) INFORMATION FOR SEQ ID NO:1:

(i) SEQUENCE CHARACTERISTICS:
        (A) LENGTH: 414
        (B) TYPE: Nucleic acid
        (C) STRANDEDNESS:  Double stranded
        (D) TOPOLOGY:   linear (ii) MOLECULE TYPE:  cDNA (iii) HYPOTHETICAL:  no (iv) ANTI-SENSE:  no (vi) ORIGINAL SOURCE:
        (A) ORGANISM:  Homo sapien
        (D) DEVELOPMENTAL STAGE:  Adult
        (F) TISSUE TYPE:  Lymphnode (vii) IMMEDIATE SOURCE:
        (B) CLONE:   Z04/hsCTLA-4/pCR3

(viii) POSITION IN GENOME:
        (A) CHROMOSOME/SEGMENT:   2q33

(ix) FEATURE:
        (A) NAME/KEY:  Human sCTLA-4 gene
        (B) IDENTIFICATION METHOD:   Found by experiment
        (D) OTHER INFORMATION:  Expresses B7 binding protein (xi) SEQUENCE DESCRIPTION:   SEQ ID NO: 1:

ATG CAC GTG GCC CAG CCT GCT GTG GTA CTG GCC AGC AGC CGA GGC        45
     Met His Val Ala Gln Pro Ala Val Val Leu Ala Ser Ser Arg Gly
      1               5                  10                  15

ATC GCC AGC TTT GTG TGT GAG TAT GCA TCT CCA GGC AAA GCC ACT        90
     Ile Ala Ser Phe Val Cys Glu Tyr Ala Ser Pro Gly Lys Ala Thr
                     20                  25                  30

GAG GTC CGG GTG ACA GTG CTT CGG CAG GCT GAC AGC CAG GTG ACT       135
     Glu Val Arg Val Thr Val Leu Arg Gln Ala Asp Ser Gln Val Thr
                     35                  40                  45

GAA GTC TGT GCG GCA ACC TAC ATG ATG GGG AAT GAG TTG ACC TTC       180
     Glu Val Cys Ala Ala Thr Tyr Met Met Gly Asn Glu Leu Thr Phe
                     50                  55                  60

CTA GAT GAT TCC ATC TGC ACG GGC ACC TCC AGT GGA AAT CAA GTG       225
     Leu Asp Asp Ser Ile Cys Thr Gly Thr Ser Ser Gly Asn Gln Va
                     65                  70                  75
```

```
        AAC CTC ACT ATC CAA GGA CTG AGG GCC ATG GAC ACG GGA CTC TAC        270
        Asn Leu Thr Ile Gln Gly Leu Arg Ala Met Asp Thr Gly Leu Tyr
                    80                  85                  90

ATC TGC AAG GTG GAG CTC ATG TAC CCA CCG CCA TAC TAC CTG GGC        315
        Ile Cys Lys Val Glu Leu Met Tyr Pro Pro Pro Tyr Tyr Leu Gl
                    95                  100                 105

ATA GGC AAC GGA ACC CAG ATT TAT GTA ATT GCT AAA GAA AAG AAG        360
        Ile Gly Asn Gly Thr Gln Ile Tyr Val Ile Ala Lys Glu Lys Lys
                    110                 115                 120

CCC TCT TAC AAC AGG GGT CTA TGT GAA AAT GCC CCC AAC AGA GCC        405
        Pro Ser Tyr Asn Arg Gly Leu Cys Glu Asn Ala Pro Asn Arg Al
                    125                 130                 135

AGA ATG TGA                                                        414
        Arg Met
```

(2) INFORMATION FOR SEQ ID NO:2:

(i) SEQUENCE CHARACTERISTICS:
       (A) LENGTH: 137
       (B) TYPE: amino acid
       (D) TOPOLOGY: linear (ii) MOLECULE TYPE:
       (A) DESCRIPTION: peptide (iii) HYPOTHETICAL: no (v) FRAGMENT TYPE: Mature Polypeptide (vi) ORIGINAL SOURCE:
       (A) ORGANISM: Homo Sapien
       (D) DEVELOPMENTAL STAGE: Adult
       (F) TISSUE TYPE: Lymphnode (ix) FEATURE:
       (A) NAME/KEY: Human sCTLA-4
       (C) IDENTIFICATION METHOD: Found by experiment
       (D) OTHER INFORMATION: Asn 76 and Asn 108 represent N-linked
          glycosylation; B7 bindi (xi) SEQUENCE DESCRIPTION: SEQ ID NO: 2:

```
        Met His Val Ala Gln Pro Ala Val Val Leu Ala Ser Ser Arg Gly
        1               5                   10                  15

Ile Ala Ser Phe Val Cys Glu Tyr Ala Ser Pro Gly Lys Ala Thr
                        20                  25                  30

Glu Val Arg Val Thr Val Leu Arg Gln Ala Asp Ser Gln Val Thr
                        35                  40                  45

Glu Val Cys Ala Ala Thr Tyr Met Met Gly Asn Glu Leu Thr Phe
                        50                  55                  60

Leu Asp Asp Ser Ile Cys Thr Gly Thr Ser Ser Gly Asn Gln Val
                        65                  70                  75

Asn Leu Thr Ile Gln Gly Leu Arg Ala Met Asp Thr Gly Leu Tyr
                        80                  85                  90

Ile Cys Lys Val Glu Leu Met Tyr Pro Pro Pro Tyr Tyr Leu Gly
                        95                  100                 105

Ile Gly Asn Gly Thr Gln Ile Tyr Val Ile Ala Lys Glu Lys Lys
                        110                 115                 120

Pro Ser Tyr Asn Arg Gly Leu Cys Glu Asn Ala Pro Asn Arg Ala
                        125                 130                 135

Arg Met
```

(2) INFORMATION FOR SEQ ID NO:3:

(i) SEQUENCE CHARACTERISTICS:
        (A) LENGTH: 614
        (B) TYPE: nucleic acid
        (C) STRANDEDNESS: Double stranded
        (D) TOPOLOGY: linear (ii) MOLECULE TYPE: cDNA (iii) HYPOTHETICAL: no (iv) ANTI-SENSE: no (vi) ORIGINAL SOURCE:
        (A) ORGANISM: Rattus Norvegicus
        (B) STRAIN: ACI
        (D) DEVELOPMENTAL STAGE: Adult
        (G) CELL TYPE: Splenocyte (vii) IMMEDIATE SOURCE:
        (B) CLONE: GG2/RsCTLA-4/pCR-3

(ix) FEATURE:
        (A) NAME/KEY: Rat sCTLA-4
        (C) IDENTIFICATION METHOD: Found by experiment
        (D) OTHER INFORMATION: Expresses putative B7 binding protein.

(xi) SEQUENCE DESCRIPTION: SEQ ID NO: 3:

```
ATG GCT TGT CTT GGA CTC CAG AGG TAC AAA ACT CAC CTG CAG CTG           45
Met Ala Cys Leu Gly Leu Gln Arg Tyr Lys Thr His Leu Gln Leu
 1               5                  10                  15

CCT TCT AGG ACT TGG CCT TTT GGA GTC CTG CTT TCT CTT CTC TTC           90
Pro Ser Arg Thr Trp Pro Phe Gly Val Leu Leu Ser Leu Leu Phe
                20                  25                  30

ATC CCA ATC TTC TCT GAA GCC ATA CAA GTG ACC CAA CCT TCA GTG          135
Ile Pro Ile Phe Ser Glu Ala Ile Gln Val Thr Gln Pro Ser Val
            35                  40                  45

GTG TTG GCC AGC AGC CAC GGT GTC GCC AGC TTT CCA TGT GAA TAT          180
Val Leu Ala Ser Ser His Gly Val Ala Ser Phe Pro Cys Glu Tyr
        50                  55                  60

GCA TCT TCA CAC AAC ACT GAT GAG GTC CGG GTG ACG GTG CTG CGG          225
Ala Ser Ser His Asn Thr Asp Glu Val Arg Val Thr Val Leu Arg
    65                  70                  75

CAG ACA AAT GAC CAA GTG ACA GAG GTC TGT GCC ACG ACA TTC ACA          270
Gln Thr Asn Asp Gln Val Thr Glu Val Cys Ala Thr Thr Phe Thr
80                  85                  90

GTG AAG AAC ACG TTG GGC TTC CTA GAT GAC CCC TTC TGC AGT GGT          315
Val Lys Asn Thr Leu Gly Phe Leu Asp Asp Pro Phe Cys Ser Gly
                95                 100                 105

ACC TTT AAT GAA AGC AGA GTG AAC CTC ACC ATC CAA GGA CTG AGG          360
Thr Phe Asn Glu Ser Arg Val Asn Leu Thr Ile Gln Gly Leu Arg
            110                 115                 120

GCT GCT GAC ACC GGA CTG ACT TTC TGC AAG GTG GAA CTC ATG TAC          405
Ala Ala Asp Thr Gly Leu Thr Phe Cys Lys Val Glu Leu Met Tyr
        125                 130                 135

CCA CCG CCA TAC TTT GTG GGC ATG GGC AAC GGG ACC CAG ATT TAT          450
Pro Pro Pro Tyr Phe Val Gly Met Gly Asn Gly Thr Gln Ile Tyr
    140                 145                 150

GTC ATC GCT AAA GAA AAG AAG TCC TCT TAC AAC AGG GGT CTA TGT          495
Val Ile Ala Lys Glu Lys Lys Ser Ser Tyr Asn Arg Gly Leu Cys
155                 160                 165

GAA AAT GCC CCC AAC AGA GCC AGA ATG TGAAAAGCAA TTTCAACCTT            542
Glu Asn Ala Pro Asn Arg Ala Arg Met
                170
```

```
    ATTTTATTCC AATCAACTGA AAGGCCATTT GTGAAGAAGA GGGAGCATTC           592

TTCAGTCTCT AAAAGCTGAG GC                                          614
```

(2) INFORMATION FOR SEQ ID NO:4:

(i) SEQUENCE CHARACTERISTICS:
        (A) LENGTH: 174
        (B) TYPE: amino acid
        (D) TOPOLOGY: linear (ii) MOLECULE TYPE:
        (A) DESCRIPTION: Polypeptide (iii) HYPOTHETICAL: no (v) FRAGMENT TYPE: Internal fragment (vi) ORIGINAL SOURCE:
        (A) ORGANISM: Rattus Norvegicus
        (B) STRAIN: ACI
        (D) DEVELOPMENTAL STAGE: Adult
        (G) CELL TYPE: Splenocyte (ix) FEATURE:
        (A) NAME/KEY: Rat sCTLA-4
        (C) IDENTIFICATION METHOD: Found by experiment
        (D) OTHER INFORMATION: B7 binding protein (xi) SEQUENCE DESCRIPTION: SEQ ID NO: 4:

```
    Met Ala Cys Leu Gly Leu Gln Arg Tyr Lys Thr His Leu Gln Leu
    1               5                   10                  15

Pro Ser Arg Thr Trp Pro Phe Gly Val Leu Leu Ser Leu Leu Phe
                    20                  25                  30

Ile Pro Ile Phe Ser Glu Ala Ile Gln Val Thr Gln Pro Ser Val
                    35                  40                  45

Val Leu Ala Ser Ser His Gly Val Ala Ser Phe Pro Cys Glu Tyr
                    50                  55                  60

Ala Ser Ser His Asn Thr Asp Glu Val Arg Val Thr Val Leu Arg
                    65                  70                  75

Gln Thr Asn Asp Gln Val Thr Glu Val Cys Ala Thr Thr Phe Thr
                    80                  85                  90

Val Lys Asn Thr Leu Gly Phe Leu Asp Asp Pro Phe Cys Ser Gly
                    95                  100                 105

Thr Phe Asn Glu Ser Arg Val Asn Leu Thr Ile Gln Gly Leu Arg
                    110                 115                 120

Ala Ala Asp Thr Gly Leu Tyr Phe Cys Lys Val Glu Leu Met Tyr
                    125                 130                 135

Pro Pro Pro Tyr Phe Val Gly Met Gly Asn Gly Thr Gln Ile Tyr
                    140                 145                 150

Val Ile Ala Lys Glu Lys Lys Ser Ser Tyr Asn Arg Gly Leu Cys
                    155                 160                 165

Glu Asn Ala Pro Asn Arg Ala Arg Met
                    170
```

(2) INFORMATION FOR SEQ ID NO:5:

(i) SEQUENCE CHARACTERISTICS:
        (A) LENGTH: 135
        (B) TYPE: nucleic acid
        (C) STRANDEDNESS: Double stranded
        (D) TOPOLOGY: Linear (ii) MOLECULE TYPE: cDNA -continued

```
    (iii) HYPOTHETICAL:  no (iv) ANTI-SENSE:  no (v) FRAGMENT TYPE:  Internal fragment (vi) ORIGINAL SOURCE:
          (A) ORGANISM:  Mus Muculus
          (B) STRAIN:  Balb/c
          (D) DEVELOPMENTAL STAGE:  Adult
          (G) CELL TYPE:  Splenocyte (ix) FEATURE:
          (A) NAME/KEY:  Mouse sCTLA-4
          (D) OTHER INFORMATION:  Asn 113 represents predicted N-linked
              glycosylation site; exp (xi) SEQUENCE DESCRIPTION:  SEQ ID NO: 5:

GTG GAA CTC ATG TAC CCA CCG CCA TAC TTT GTG GGC ATG GGC AAC          45
    Val Glu Leu Met Tyr Pro Pro Pro Tyr Phe Val Gly Met Gly Asn
    1               5                   10                  15

GGG ACG CAG ATT TAT GTC ATT GCT AAA GAA AAG AAG TCC TCT TAC          90
    Gly Thr Gln Ile Tyr Val Ile Ala Lys Glu Lys Lys Ser Ser Tyr
                    20                  25                  30

AAC AGG GGT CTA TGT GAA AAT GCC CCC AAC AGA GCC AGA ATG TGA         135
    Asn Arg Gly Leu Cys Glu Asn Ala Pro Asn Arg Ala Arg Met
                    35                  40

(2) INFORMATION FOR SEQ ID NO:6:

(i) SEQUENCE CHARACTERISTICS:
          (A) LENGTH:  44
          (B) TYPE:  amino acid
          (D) TOPOLOGY:  linear (ii) MOLECULE TYPE:
          (A) DESCRIPTION:  carboxyl terminal fragments containing
              alternative splice junction (iii) HYPOTHETICAL:  no (vi) ORIGINAL SOURCE:
          (A) ORGANISM:  Mus Muculus
          (B) STRAIN:  Balb/c
          (D) DEVELOPMENTAL STAGE:  Adult
          (G) CELL TYPE:  Splenocyte (ix) FEATURE:
          (A) NAME/KEY:  Mouse sCTLA-4
          (D) OTHER INFORMATION:

(xi) SEQUENCE DESCRIPTION:  SEQ ID NO: 6:

Val Glu Leu Met Tyr Pro Pro Pro Tyr Phe Val Gly Met Gly Asn
      1               5                   10                  15

Gly Thr Gln Ile Tyr Val Ile Ala Lys Glu Lys Lys Ser Ser Tyr
                      20                  25                  30

Asn Arg Gly Leu Cys Glu Asn Ala Pro Asn Arg Ala Arg Met
                      35                  40

(2) INFORMATION FOR SEQ ID NO:7:

(i) SEQUENCE CHARACTERISTICS:
          (A) LENGTH:  20
          (B) TYPE:  nucleic acid
          (C) STRANDEDNESS:  single stranded
          (D) TOPOLOGY:  linear (xi) SEQUENCE DESCRIPTION:  SEQ ID NO: 7:

CATGGCTTGT CTTGGACTCC                                                20
```

(2) INFORMATION FOR SEQ ID NO:8:

(i) SEQUENCE CHARACTERISTICS:
        (A) LENGTH: 20
        (B) TYPE: nucleic acid
        (C) STRANDEDNESS: single stranded
        (D) TOPOLOGY: linear (xi) SEQUENCE DESCRIPTION: SEQ ID NO: 8:

GCCTCAGCTT TTAGAGACTG                                              20

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single stranded
        (D) TOPOLOGY: linear (xi) SEQUENCE DESCRIPTION: SEQ ID NO: 9:

TTCCTGAAGA CCTGAACACC                                              20

(2) INFORMATION FOR SEQ ID NO:10:

(i) SEQUENCE CHARACTERISTICS:
        (A) LENGTH: 20
        (B) TYPE: nucleic acid
        (C) STRANDEDNESS: single stranded
        (D) TOPOLOGY: linear (xi) SEQUENCE DESCRIPTION: SEQ ID NO: 10:

AGAATTGCCT CAGCTCTTGG                                              20

(2) INFORMATION FOR SEQ ID NO:11:

(i) SEQUENCE CHARACTERISTICS:
        (A) LENGTH: 20
        (B) TYPE: nuclic acid
        (C) STRANDEDNESS: single stranded
        (D) TOPOLOGY: linear (xi) SEQUENCE DESCRIPTION: SEQ ID NO: 11:

TGACACCGGA CTGTACTTCT                                              20

(2) INFORMATION FOR SEQ ID NO:12:

(i) SEQUENCE CHARACTERISTICS:
        (A) LENGTH: 20
        (B) TYPE: nucleic acid
        (C) STRANDEDNESS: single stranded
        (D) TOPOLOGY: linear (xi) SEQUENCE DESCRIPTION: SEQ ID NO: 12:

TCACTATCCA AGGACTGAGG                                              20

(2) INFORMATION FOR SEQ ID NO:13:

(i) SEQUENCE CHARACTERISTICS:
        (A) LENGTH: 20
        (B) TYPE: nucleic acid
        (C) STRANDEDNESS: single stranded
        (D) TOPOLOGY: linear (xi) SEQUENCE DESCRIPTION: SEQ ID NO: 13:

TCACATTCTG GCTCTGTTGG                                              20